(12) United States Patent
Foulon et al.

(10) Patent No.: US 9,949,729 B2
(45) Date of Patent: Apr. 24, 2018

(54) SURGICAL RETRACTOR SYSTEMS

(71) Applicant: MEDENVISION, Leuven (BE)

(72) Inventors: Wouter Foulon, Leuven (BE);
Bastiaan Winnelinckx, Leuven (BE);
Kristoff Corten, Herselt (BE)

(73) Assignee: MEDENVISION, Leuven (BE)

( * ) Notice: Subject to any disclaimer, the term of this patent is extended or adjusted under 35 U.S.C. 154(b) by 577 days.

(21) Appl. No.: 14/367,974

(22) PCT Filed: Dec. 20, 2012

(86) PCT No.: PCT/EP2012/076528
§ 371 (c)(1),
(2) Date: Jun. 23, 2014

(87) PCT Pub. No.: WO2013/092938
PCT Pub. Date: Jun. 27, 2013

(65) Prior Publication Data
US 2015/0011836 A1  Jan. 8, 2015

(30) Foreign Application Priority Data

Dec. 21, 2011  (BE) .................... 2011/0746

(51) Int. Cl.
*A61B 17/02* (2006.01)
*A61B 1/32* (2006.01)
*A61B 46/00* (2016.01)
*A61B 17/00* (2006.01)

(52) U.S. Cl.
CPC ............ *A61B 17/02* (2013.01); *A61B 1/32* (2013.01); *A61B 17/0293* (2013.01); *A61B 46/00* (2016.02); *A61B 2017/00473* (2013.01); *A61B 2017/0287* (2013.01)

(58) Field of Classification Search
CPC ... A61B 1/32; A61B 17/02; A61B 2017/0287; A61B 17/0293
See application file for complete search history.

(56) References Cited

U.S. PATENT DOCUMENTS 4,622,955 A * 11/1986 Fakhrai ................. A61B 17/02
                                                              600/217
5,938,592 A *  8/1999 Koteles ................. A61B 17/02
                                                              600/227
6,547,725 B1    4/2003 Paolitto et al.
(Continued)

FOREIGN PATENT DOCUMENTS

| JP | H09253086 A | 9/1997 |
| WO | 2000009017 A1 | 2/2000 |
| WO | 2007146830 A2 | 12/2007 |

OTHER PUBLICATIONS

Belgium Search Report for corresponding Belgium Application No. 2011/0746, completed Aug. 15, 2012.
(Continued)

*Primary Examiner* — Larry E Waggle, Jr.
(74) *Attorney, Agent, or Firm* — Workman Nydegger (57) ABSTRACT

A medical device for keeping open of a wound during surgery is described. It comprises a surgical retractor, a mechanical retracting system a force element for automatically winding an elongate wire-like element to apply tension to the elongate wire-like element.

16 Claims, 6 Drawing Sheets

(56) References Cited

U.S. PATENT DOCUMENTS

| | | | |
|---|---|---|---|
| 7,691,058 B2* | 4/2010 | Rioux | A61B 17/0293 |
| | | | 600/231 |
| 8,007,515 B2 | 8/2011 | Paolitto et al. | |
| 8,377,096 B2 | 2/2013 | Paolitto et al. | |
| 2003/0139776 A1 | 7/2003 | Paolitto et al. | |
| 2004/0186356 A1 | 9/2004 | O'Malley et al. | |
| 2007/0179511 A1 | 8/2007 | Paolitto et al. | |
| 2007/0293730 A1 | 12/2007 | Rioux et al. | |
| 2008/0234551 A1 | 9/2008 | Lin et al. | |
| 2010/0145153 A1* | 6/2010 | Rioux | A61B 17/0293 |
| | | | 600/208 |
| 2011/0270283 A1 | 11/2011 | Paolitto et al. | |

OTHER PUBLICATIONS

International Search Report for corresponding International PCT Application No. PCT/EP2012/076528, dated May 6, 2013.
Japanese Office Action from JP Application No. 2014-548044, dated Nov. 22, 2016. 4 Pages.
Australian Examination Report from AU Application No. 2012356942, dated Apr. 7, 2017, 4 Pages.
Japanese Office Action from JP Application No. 2014-548044, dated Jan. 7, 2017.
Chilean Office Action from CL Application No. 201401678, dated Jun. 20, 2014.

* cited by examiner

SURGICAL RETRACTOR SYSTEMS

FIELD OF THE INVENTION

The present invention relates to systems for use with surgical procedures as well as to the use of such systems. More particularly, the present invention relates to methods for keeping open a wound during surgery as well as to devices and systems for assisting in opening a wound during surgery.

BACKGROUND OF THE INVENTION

During open surgery (i.e. typically not for minimally invasive surgery), the incision through which surgical procedures are to be performed needs to be expanded and kept open in order to provide to the surgeon sufficient access to the surgical site for performing the procedure. Typically, surgical retractors are used for this, i.e. elements for expanding the edges of the incision for keeping the wound open. Usually, such retractors are made of steel. During surgery, typically supporting staff of the surgeon assist by handling the surgical retractors for expanding the incision to keep the wound open.

Some surgical retracting systems are known wherein the surgical retractors need to be connected to supports such as specifically developed surgical tables, stands mounted to a surgical table, etc.

One example of a system that allows expanding an incision to keep open a wound is described in U.S. patent application 2008/234551 (A1). The document describes a system for abdominal surgery, in which a number of external fixation points for retractors are provided by means of rods directly or indirectly mounted to the surgical table. Surgical retractor elements are then attached to springs to pull the wound open. The system has the disadvantage that installation is relatively complex and that manipulation at different sides of the patient is required.

There is a need for a more efficient system and a more efficient method for expanding wounds for providing access to the surgical site.

SUMMARY OF THE INVENTION

It is an object of embodiments of the present invention to provide good devices, systems and methods are provided for keeping open a wound, for example during surgery.

It is an advantage of embodiments according to the present invention that a surgical retractor system is provided which allows keeping open a wound in a correct way during surgery or cosmetic surgery.

It is an advantage of embodiments according to the present invention that a surgical retractor system is provided which can easily applied in a plurality of different types of surgery, such as for example during DAA (direct anterior approach) hip surgery.

It is an advantage of embodiments according to the present invention that surgical retractors are provided as well as methods of using them that inherently allow accurate positioning of the surgical retractors.

It is an advantage of embodiments according to the present invention that systems are provided which are able to correctly expand an incision for keeping open a wound and that can be used and manipulated from the location where the surgeon wishes to perform the surgical procedure with little or no further assistance of supporting staff being required. It is thus an advantage of embodiments according to the present invention that a surgical retractor system is provided that allows application and manipulation of the surgical refractor system for keeping open the wound near the location where the surgeon is performing the surgery, so that the system can accurately be used through manipulation by only a small number of individuals, or even through manipulation by a single person only.

It is an advantage of embodiments according to the present invention that the surgical retractor system during use automatically ensures accurate tension on the edges of the incision or wound, without any additional efforts being required by the surgeon.

It is an advantage of at least some embodiments of the present invention that providing tension can be performed automated and/or automatically using a differential winding system, allowing an accurate and good orientation of the retractor during surgery.

It is an advantage of at least some embodiments of the present invention that user-friendly systems are provided, as manipulation of the surgical retractor system can completely take place at or close to the surgical retractors.

The above-mentioned objective is accomplished by a device, apparatus and/or method according to the present invention.

The present invention relates to a medical device for keeping open a wound during surgery, the medical device comprising a surgical retractor provided with an element, for placing at an edge of a wound or tissue, a mechanical retracting system arranged for coupling to or forming part of the retractor, wherein the mechanical retracting system comprises a force element for automatically retracting an elongate wire-like element to apply tension to the elongate wire-like element.

The mechanical retracting system may be provided with at least one control element for activating and/or deactivating the automatically retracting. The mechanical retracting system may comprise a differential retracting system.

According to embodiments of the present invention, the mechanical retracting system may be a mechanical winding system. The mechanical winding system may comprise at least one spool for winding the elongated wire-like element, wherein the at least one spool is provided with a force element for automatically winding the elongate wire-like element to apply tension to the elongate wire-like element.

The element for placing at an edge of a wound or tissue may be a hook shaped, angle shaped or curved element for placing around an edge of the wound or the tissue. Alternatively the element may have a ring shape. A further alternative is that the element is adapted for engaging with the edge of the wound or the tissue, e.g. by incorporating a clamp or a sticking element for engaging with the edge.

It is an advantage of a medical device according to an embodiment of the present invention that providing the tension on the elongate wire-like element for orientating the surgical retractor accurately can be performed by controlling the control element located on the winding system, and that, therefore, simple manipulation by the surgeon can be performed from a site at which the surgical procedure is performed by the surgeon. The elongated wire-like element may be adapted to connect the winding system with an external fixation point.

The winding system may comprise a differential winding system. The differential winding system may induce differential tension by inducing a tension force from more than one direction.

The winding system may comprise more than one spool, whereby each spool may be adapted for winding an elongate wire-like element, the element being suitable for the connection of the winding system to an external fixation point, so that by using more than one spool, the orientation of the refractor with respect to the wound can be controlled.

The winding system may comprise, for each spool, a force element. The force element may be a torsion spring. The force element may be a micro-electromechanical system. The at least one control element may comprise a control point on the retractor or on the mechanical retracting system for activating and/or deactivating the automatically retracting. In some embodiments, the at least one control element may be a control element arranged for simultaneously controlling the automatically winding of different spools.

The at least one control element may comprise a set of control element, each control element being adapted for controlling the automatically winding of a spool.

The control element may comprises at least one of the group of a clamp for clamping the elongate wire-like element, a blocking element that interferes with the mechanical retracting system, e.g. with the spool or the force element, for preventing automatically retracting, e.g. winding, or a coupling mechanism for detachably coupling the force element and the spool.

The mechanical retracting system and the surgical retractor may be two distinct elements which can be coupled to one another and which together form a kit of parts of the medical device.

The winding system in some embodiments may be arranged such that, when coupled to the surgical retractor, the spool is positioned between the surgical retractor and an unwound portion of the elongated wire-like element.

The winding system may be arranged such that, when coupled to the surgical retractor, an unwound portion of the elongated wire-like element is positioned between the surgical retractor and the spool.

The surgical retractor and the winding system may each have a coupling element for detachably coupling to one another.

The winding system may be embedded in the surgical retractor.

The medical device may furthermore comprise an indication mechanism for indicating information regarding the use of the surgical retractor during a set of successive steps of a surgical procedure. The indication mechanism may be configured for indicating whether for a particular step, the surgical retractor is to be used, the surgical retractor is to be used in combination with another surgical retractor, the orientation wherein the surgical retractor is to be used and/or which external fixation points are to be used.

The winding system may comprise at least a spool for winding an elongated wire-like element that can connect the winding system to an external fixation point.

The winding system may comprise a housing for containing the at least one spool and the housing may comprise at least one opening through which the elongated wire-like element can pass.

The present invention furthermore relates to a method for keeping open of a wound during surgery, the method comprising selecting a medical device as described above, fixing the medical device, e.g. to at least one external fixation point, activating the automatically retracting, e.g. winding, and positioning the element of the retractor at an edge of the wound or the tissue, and de-activating the automatically retracting, e.g. winding, after the retractor is positioned correctly.

Positioning the element may comprise positioning a hook shaped, angle shaped or curved element of the retractor around an edge of the wound or the tissue. Positioning the element may comprise positioning a ring shaped element. Positioning the element may comprise engaging with the edge of the wound or the tissue, e.g. using a clamp or a sticking element.

The method may furthermore comprise handling the medical device and activating the retracting, e.g. automatically winding, re-orienting the medical device, and after re-orienting the medical device correctly, deactivating the automatically retracting, e.g. winding, and releasing the retractor.

The present invention also relates to the use of a medical device as described above, for keeping open a wound during surgery.

The present invention also relates to a mechanical retracting system configured for connecting a surgical retractor with an external fixation point for keeping open a wound during surgery, wherein the mechanical retracting system can be coupled to or is forming part of the surgical retractor. The retracting system, e.g. winding system, may comprises a force element for automatically retracting an elongated wire-like element. In some embodiments, the retracting system may be a winding system comprising at least one spool for winding an elongated wire-like element, wherein the at least one spool is provided with a force element for automatically winding the elongate wire-like element to bring the elongated wire-like element under tension. The mechanical retracting system, e.g. winding system, may be provided with at least one control element for activating and/or deactivating the automatically retracting, e.g. winding.

The present invention also relates to a set of medical devices for keeping open a wound during surgery, wherein at least one of the medical devices is a medical device as described above.

The present invention also relates to a retractor coupleable to a mechanical retracting system, e.g. winding system, as described above, whereby the retractor comprises coupling means for detachably coupling it to a mechanical retracting system as described above.

The present invention also relates to a surgical drape for sterile covering of the legs and abdomen of a surgical procedure, the surgical drape comprising a first part provided with two leg-shaped portions and a second portion provided with an incision window, wherein the second portion is arranged with respect to the first portion of the window such that the incision window covers at least partly, and advantageously completely, the abdomen region and the inguinal region, when the legs—e.g. upper legs—of a patient that needs to undergo the surgery are positioned in the leg-shaped portions of the surgical drape. The surgical drape thereby may be fully or maximally folded open.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIGS. 8 to 10 illustrate a medical device whereby the surgical retractor and the winding system are adapted for releasably engaging with each other, whereby

The drawings are only schematic and are non-limiting. In the drawings, the size of some of the elements may be exaggerated and not drawn on scale for illustrative purposes. The dimensions and the relative dimensions do not correspond to actual reductions to practice of the invention.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to a retractor, reference is made to a surgical device that allows the surgeon to keep open a wound or to keep organs or tissue in a certain position, so that portions of the body that are beneath or behind these organs or tissues become or remain accessible.

Figure 1:
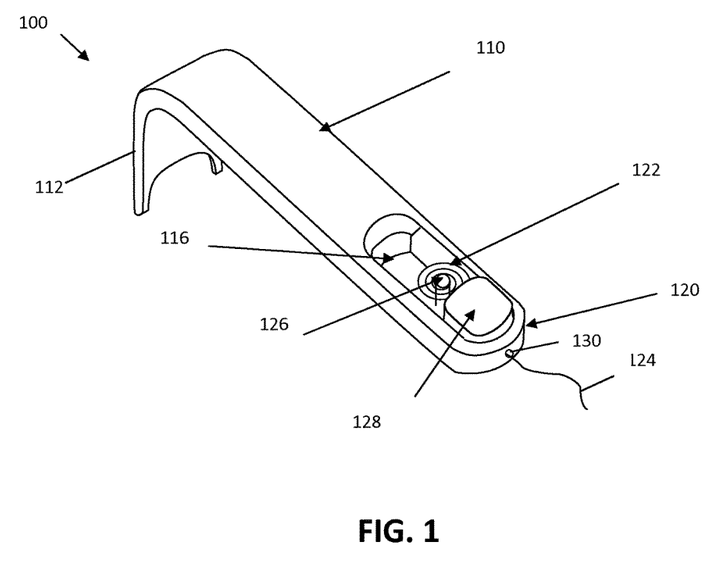
FIG. 1 illustrates a medical device including a surgical retractor and winding system configured for automatically winding according to an embodiment of the present invention.

In a first aspect, the present invention relates to a medical device for keeping open a wound during surgery. The technique of keeping open a wound during surgery is also often referred to as retracting edges of a wound. Embodiments of the present invention can be used in various types of surgery, such as for example, in thoracic surgery, cardiovascular surgery, abdominal surgery, urological surgery, gynecological surgery, foot-hand-shoulder-back surgery, eye surgery, stomatological surgery, ENT surgery (nasal throat-ear), hip surgery, etc. One example of hipsurgery is direct anterior approach hip surgery. The medical device according to embodiments of the present invention may be provided as a single component, or may be provided from a variety of separate components which together form a kit of parts. By way of illustration, embodiments of the present invention not being limited thereto, standard and optional components of the medical device are illustrated in FIG. 1.

According to embodiments of the present invention, the medical device 100 comprises a retractor 110. A retractor 110 typically may comprise a hook-shaped, angle-shaped or curved element or member 112 to be positioned around an edge of the wound or around tissue, so that using the retractor 110, once positioned accurately, a wound can be kept open and/or tissue can be positioned to make underlying body portions accessible during surgery. Alternatively the retractor also could have a ring shaped element e.g. for positioning in an incision made in the abdomen. Another alternative may be that the element comprises an engaging means for engaging with the edge of the wound or the tissue. Such an engaging means may e.g. be a clamping element or a sticking element. In general, the retractor may be provided with an element for placing at an edge of a wound or tissue. The retractor 110 may be made from any suitable material. While at present frequently metals, such as steel, are used, the invention is not limited thereby and the retractor can also be made of a plastic, a polymer-based material, etc. The choice of material to be used can be made such that the cost of the retractor 110 is sufficiently low that the medical device 100 can be considered as consumable. Specific examples of plastic materials that can be used are Tecanyl MT, Tecaform AH MT or Tecapro MT, but it will be clear to the skilled person that embodiments are not limited thereby. The refractor can have different shapes and sizes. In some cases retractors can be provided that are more generally applicable for different types of wounds/incisions which must be kept open. In other cases the retractors also may have a specific shape so that the retractor is mainly or only applicable for surgical procedures through a specific type of wound or incision.

In more advanced embodiments, additional elements can be added for assisting during surgery. Examples of such additional elements can be suction elements for keeping the wound dry or assisting thereby, lighting elements for illuminating the wound or assisting therein, etc. (not shown in FIG. 1).

According to embodiments of the present invention, the medical device 100 also comprises a mechanical retracting system 120 arranged for coupling to or forming part of the retractor 110, wherein the mechanical retracting system 120 comprises a force element 126 for automatically retracting an elongate wire-like element. Whereas embodiments further will be illustrated with reference to a retractor being a winding system 120 comprising a spool and force element for automatically winding an elongage wire-like element, which is a particularly advantageous embodiment, embodiments of the present invention are not limited thereto. For example, the mechanical retracting system 120 may comprise an internal fixation point and an elongate wire-like element connected to the internal fixation point such as a telescopic, stretching or spring-like element, that can extend in length by providing a pulling force to it, and that automatically shortens, when no further force is applied. Mechanical equivalents, also allowing automatically retracting of a wire-like element are also envisaged.

As announced above, embodiments of the present invention further will be illustrated by means of a retracting system comprising a winding system 120, whereby features and advantages can be mutates mutandis applied to mechanical refracting systems based on equivalent principles. In some embodiments, such a mechanical winding system 120 is embedded in the retractor 110, i.e. the retractor 110 and the mechanical winding system always form a single piece for the user. The mechanical winding system 120 may for example be embedded on that side of the retractor 110 that is positioned away from the hook-shaped, angle-shaped or curved element 112, i.e. that side of the refractor 110 that is furthest away from the wound. The mechanical winding system 120 can be hidden in the interior of the retractor 110, for example in a cavity 116. This does not only provide an aesthetic advantage, but can also ensure that the components of the mechanical winding system 120 do not become dirty or damaged during use.

Figure 2:
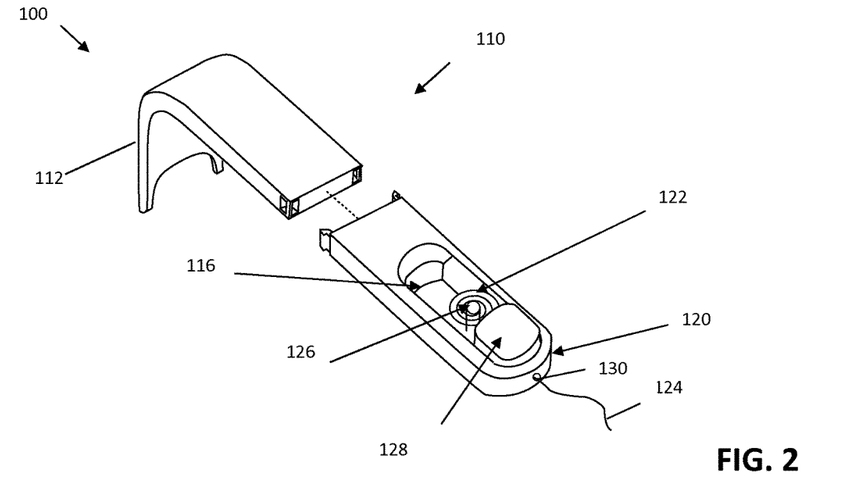
FIG. 2 illustrates a medical device with interconnectable but separate surgical retractor and winding system configured for automatically winding according to another embodiment of the present invention.
Figure 8:
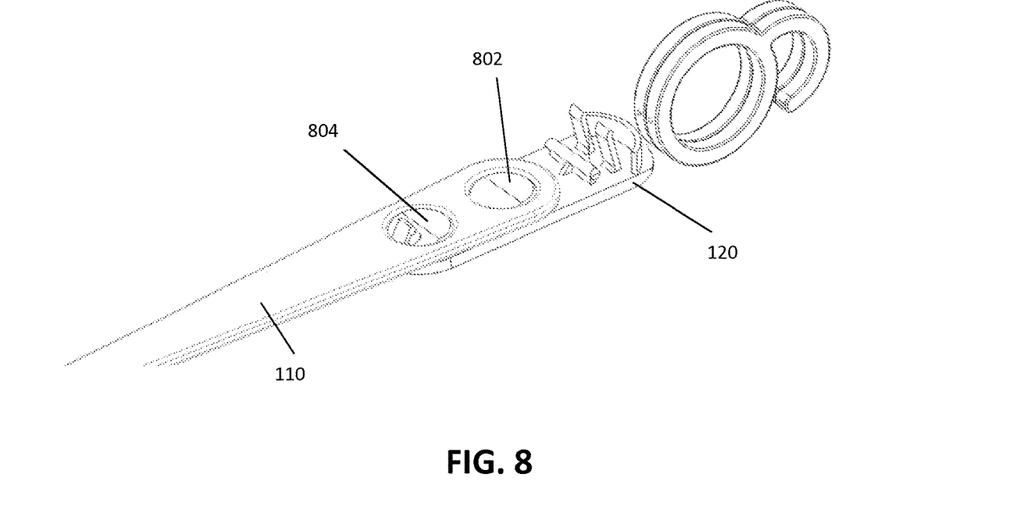
FIG. 8 illustrates the retractor positioned with respect to part of the winding system.
Figure 9:
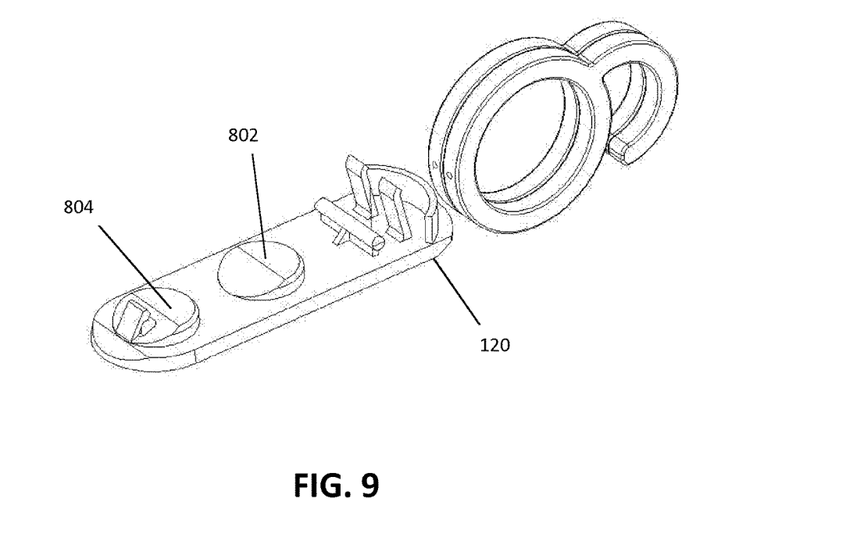
FIG. 9 illustrates only part of the winding system.
Figure 10:
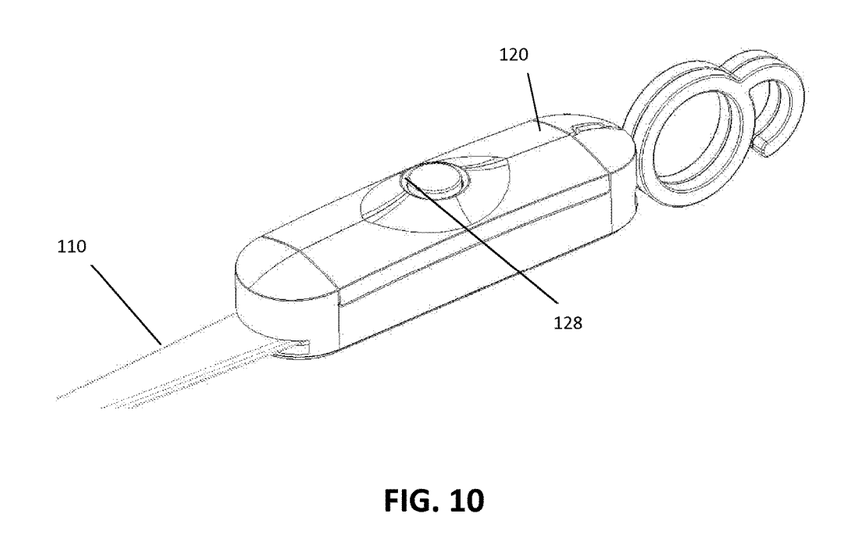
FIG. 10 illustrates the full engaged retractor and winding system, according to embodiments of the present invention.

Alternatively, in some embodiments, the winding system 120 is a separate element that can be coupled to the retractor 110, e.g. as shown in FIG. 2. Such connection or coupling can be done in any suitable manner, such as using a click system, using a clip connection, using a fixation system, through a glue connection or using any other connection allowing connecting the retractor to the winding system. In some embodiments, this coupling or connection can be a rigid coupling, i.e. a coupling so that—e.g. after initial connection—the winding system 120 and the retractor 110 cannot undergo a substantial relative movement with respect to each other. By way of illustration, embodiments of the present invention not being limited thereto, a particular example of coupling means for detachably coupling the retractor 110 and the winding system 120 to each other is illustrated in FIG. 8 to FIG. 10. FIG. 8 illustrates part of the winding system and part of the refractor in coupled arrangement. In the present example the coupling means on the retractor is a set of two holes and the coupling means on the winding system comprises a set of two protruding portions 802, 804 suitable for fitting the holes in the retractor. An additional clippable element can be provided for clipping the retractor and the winding system to more firmly couple to each other. In the example shown, a system having a double spool for applying differential tension on the refractor is illustrated in FIG. 9. In the exemplary embodiments, the winding system is located in the immediate vicinity of the retractor 110, or even is embedded therein.

According to one set of embodiments of the present invention, the winding system 120 comprises at least one spool 122, which could also be referred to as a coil, for the winding of a single elongated wire-like—also referred to as wire-shaped—element. This elongate element can be suitable for connecting the winding system with one or more external fixation points. In other cases, another portion of the winding system may be adapted with a connection piece for connecting to one or more external fixation points. Such a connection piece may for example be part of a hook-eye connecting element, a clickable connection, a clipable connection, a connection based on winding of an elongated element, etc. The elongate wire-like element 124 may be for example, a rope, a wire, a chain or a ribbon. Such an elongate wire-like element 124 may be made of a suitable material that is sufficiently strong to keep the surgical retractor 110 under tension so that during the surgery, the surgical retractor 110 is positioned and oriented in the desired direction.

The provision or reduction of unwound elongate wire-like element 124 may be based on rotation of the spool, although other mechanical equivalents also are envisaged within the scope of the claims. For example, the spool may have a shifting system for shifting components of the core of the spool. By shifting components of the core of the spool, the perimeter of the spool can be changed, e.g. enlarged, and the amount of unwound wire-like element 124 can be reduced.

The at least one spool 122 may advantageously be incorporated in a piece of the retractor 110, or in the winding system 120. The at least one spool 122 may be incorporated in a housing. The elongated wire-like element 124 may for example be guided through one or more special openings 130 in the housing for leaving the retractor or the winding system. The external fixation point 150 to which the elongate wire-like element or the winding system can be connected during operation may, for example, be a point in the environment, a point on the operating table, a point on a tripod or other element that is directly or indirectly connected to or in the vicinity of the operating table, a point on the patient, etc. In some embodiments, the external fixation point is a point in a surgical drape that is used during the operation, as described in a separate aspect of the present invention.

According to embodiments of the present invention, the spool 122 comprises a force element 126 for the automatically winding of the elongated wire-like element 124 to apply or induce tension to this element. The force element 126 thus may be built into the spool, or may be connected to the spool 122. Alternatively the force element 126 may cooperate with the spool 122, so that a particular configuration is ensured wherein the elongate wire-like element 124 is kept under tension. Such a force element may be a torsion spring which ensures that there is an automatic mechanical winding of the elongated wire-shaped element 124, when it is not under tension. Alternative force elements can also be used, such as for example other types of springs, etc. Still another alternative force element may be a micro-electro-mechanical system (MEMS), such as e.g. a MEMS motor, for inducing a force on the elongate wire-like element.

According to embodiments of the present invention, the winding system also advantageously may comprise a control element 128 for activating and/or de-activating the automatically winding, i.e. for activating and/or de-activating the winding and thus inducing tension on the rope. By way of illustration, an example of such an embodiment is shown in FIG. 10. The control element 128 may for example be an element that controls the coupling between the force element and the spool and in this way controls the automatically winding, or may for example be an element that controls the movement of the elongate element and in this way controls the automatically winding. In the first case, the control element 128 can be a coupling system for controlling the coupling between the spool and the force element. This can for example be done by shifting one of the components relative to the other component(s). In this case, the force element and the spool are detachably engageable with each other, and the link is controlled by the control element 128. In the second case, the control element 128 can be a clamp for clamping the elongate element and thus blocking it. The control element 128 may alternatively be an additional blocking element that interferes with the spool 122 or the force element 126, and thereby prevents that automatically winding occurs.

The control element 128 may include a manipulating point for activating and/or deactivating the automatically winding. It is an advantage of at least some embodiments of the present invention that the automatically winding can be controlled at or close to the retractor 110, so that correct positioning of the refractor 110 can be performed by the surgeon at the location where the surgical procedure is performed so that additional staff is not or nearly not required.

When the control element 128 has activated automatically winding, this does not only imply that automatically winding occurs of the elongated wire-like element for bringing it to tension, but it also permits the elongated wire-like element 124 for unwinding from the spool 122 when a pulling force is applied to the elongated wire-like element 124.

Figure 3A:
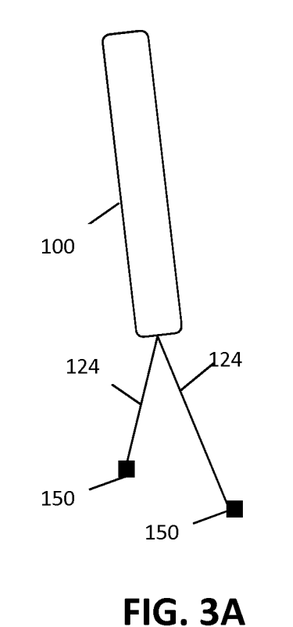
FIG. 3 illustrates the orientation of a medical device making use of a differential winding system according to an embodiment of the present invention.
Figure 3B:
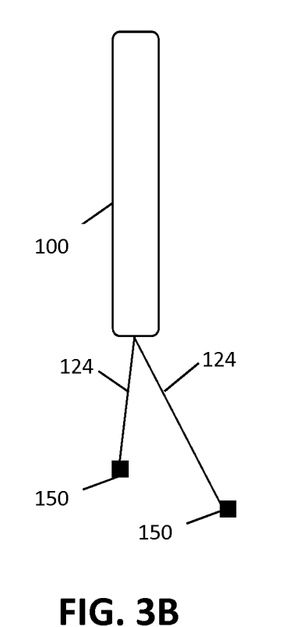

In some specific embodiments of the present invention, the winding system 120 may comprise more than one spool 122 and more than one corresponding elongated wire-shaped element 124. In advantageous embodiments, each of the more than one spools 120 comprises a force element 126. These spools and/or force elements can be positioned on top of each other or next to each other. One control element 128 may be provided for activating and/or deactivating some or all of the spools 122. In other words, the one control element 128 may control two or more spools 122 of the winding system 120 so that the elongate wire-like elements 124 can adapt to a new position or orientation of the retractor 110. Alternatively, more than one or all of these spools 122 can be provided with a control element 128 for controlling the automatically winding of each of the spools individually. This may for example be the case for spools that are oriented in different directions outside of one and the same plane, e.g. also referred to as oriented in 3D. In addition, embodiments of the present invention are not limited to systems with only spools that are automatically winding, but can also contain at least some spools that are not automatically winding. In a specific embodiment, the winding system 122 comprises two spools 120, each with an elongate wire-like element 124, a force element 126, and a control element 128. An advantage of this embodiment is that the retractor 110 can be oriented by bringing the two elongated wire-like elements 124 under tension, more specifically, for example, by controlling the unwound length of the two elongate wire-shaped elements. By way of illustration, FIG. 3A and FIG. 3B show a schematic representation of how selecting the appropriate length of the two elongated wire-like elements 124 can determine the orientation of the retractor 110. It is clear from the drawings that a difference in length of the two elongated wire-like elements induces a different orientation of the retractor. A similar effect is obtained when more than two elongate wire-like elements 124 are used (i.e. guidance in more than two directions).

The winding system 120 thus can be a differential winding system, whereby different spools can be used so that differential forces are induced and different positions and orientations of the refractor 110 can be obtained. The different vectors of traction forces induced by the differential winding system and the force by which the retractor 110 retracts the edge of the wound or tissue balance each other.

According to embodiments of the present invention, the control element can be adapted for allowing the winding system 120 to adapt to a new position by free automatically winding, when the retractor 110 is positioned in the desired position, and to subsequently limit further automatic winding of the winding system thus making sure that the desired position of the retractor is maintained.

The control element 128 can thus be adapted such that during surgery the force mechanism can be uncoupled, can be repositioned and can again be fixed for safeguarding another position with a certain fraction direction. By using different spools, different traction directions can be used for obtaining the same resulting force on the retractor 110 so that it is kept in the desired position and orientation.

It is an advantage of embodiments as described above, that a self-retracting medical device 100 can replace the need for a medical assistant. Where in the past, the assistant needed to ensure the fixation of the retractor 110 at certain specific positions, depending on the requirements of the operation, and the assistant needed to ensure an accurate displacement and fixation, this can now, by means of embodiments of the present invention, be done by the surgeon who can move the retractor 110 by hand after the activation of the winding system, and who can deactivate the winding system, once the retractor is positioned correctly. It is an advantage of at least some embodiments that an accurate and easy manipulation can be obtained by manipulating the retractor 110 and by manipulating one or more control elements of the retractor 110 so that the retractor 110 can be repositioned without the need for an assistant and while no significant additional effort or loss of flexibility occurs. It is an advantage of embodiments of the present invention that there is less need for assisting personnel, which may allow more efficient surgery, as well in terms of economic cost as in terms of salary costs. Positioning of a same retractor 110 in consecutive different positions and/or with different traction directions is simple using the above device 100. In addition, the medical device 100 can reduce the required number of external fixation points without loss of stability in the traction provided.

It is also an advantage that the system is adaptable to different surgical situations, such as for example surgery on less muscular or more muscular patients, or surgery on fatter or skinnier patients. In these different situations, the retractor needs to keep open the wound in different directions or the retractor needs to retract different tissues, which is easily possible with embodiments of the present invention.

It is an advantage of embodiments according to the present invention that the number of retractors to be used can be limited and that the retractors can be manufactured in disposable material so that for example there is a reduction in sterilization and logistics costs.

It is an advantage according to at least some embodiments of the present invention that the retractor can be fixed in different traction directions in a smooth manner by a single person. The person handling the retractor system can first fix the retractor to different external fixation points 150 (e.g. before or at the start of the operation), and can then, during the surgical procedure, bring the retractor in the desired position or sequential desired positions by activating and deactivating the traction on the retractor itself. The retractor can thus be fixed in the respective orientations envisaged by the surgeon. Moreover, the system allows that a single person can manipulate different fixation systems during a single surgery, e.g. simultaneously.

Figure 4:
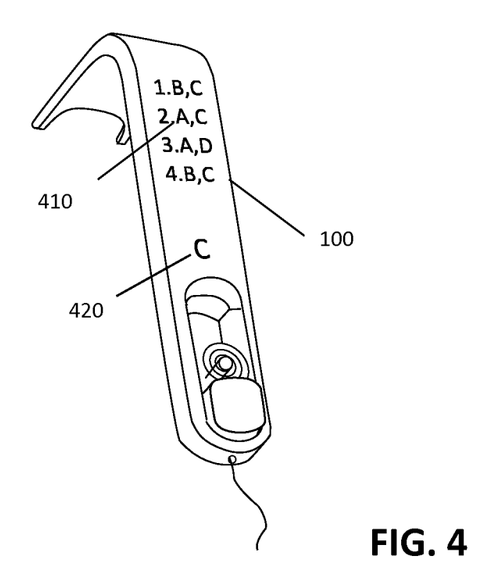
FIG. 4 illustrates a medical device with an indicator system for using surgical retractors, according to one embodiment of the present invention.
Figure 11:
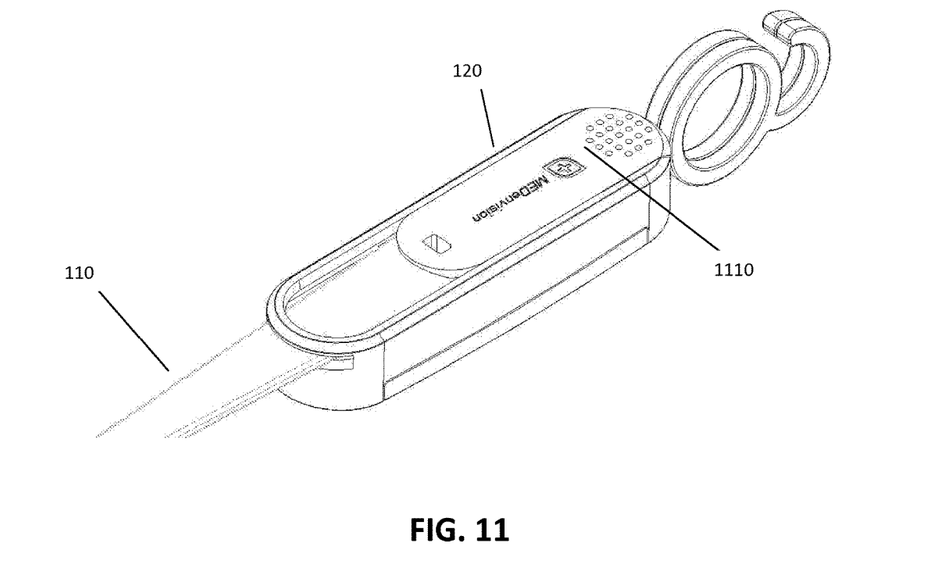
FIG. 11 illustrates a releasably engaged retractor and winding system, whereby the winding system comprises an indication system according to an embodiment of the present invention.

In a particular embodiment of the present invention, the medical device 100 comprises an indication system for indicating the specific use of the retractor 110 during the surgical procedure. Optimally keeping open the wound for surgery can normally be performed by applying a sequence of different retracting situations wherein certain retractors in certain orientation should be used. According to a specific embodiment of the present invention, a retractor 110 can contain an indication system for indicating, for a set of successive steps during a surgical procedure, information about the use of the refractor 110. The indicator system can, for example, for each of the steps of keeping open the wound during surgery, indicate whether the retractor is to be used, in combination with which other retractor(s) the retractor is to be used, in which orientation the retractor is to be used, which external fixation points are to be used, etc. The indicator system may for example be based on visual, auditive or audiovisual indication. This can be done via an indication system with color code, by an indication system with a symbol code, by an indication system where the use is auditory indicated for example, via a speaker, via an indication system where the use is indicated via a display, etc. The different retractors that need to be used during a surgical procedure can for example have a specific color or symbol code, for example, indicated on the handle. The indication system can display all the steps in a single list or show the different steps successively, making it easier for the surgeon to avoid mistakes. Sequentially indicating the different steps can be done in a manual mode, whereby the surgeon in each further step wherein a different retracting of the wound is required, adjusts the indication in the indication system. Alternatively, the indication system can also be semi-automatically or automatically, wherein, e.g. on the basis of an algorithm, the next step for the wound retracting process is indicated. By way of illustration, FIG. 4 illustrates an example of an indication system in the form of a summary table 410 which is indicated on a retractor 100. In some examples, such information can be indicated on the different retractors of a set of medical retractors for performing a particular type of surgery. Furthermore, also an identification 420 of the retractor itself can be indicated. The various retractors are in the present example, identified by a code. For the given example, 4 different retracting situations are required, wherein in the first step use is made of retractors B and C, in the second step of retractors A and C, in a third step of retractors A and D, and in a fourth step again of retractors B and C. In FIG. 11 another example of a medical device according to an embodiment of the present invention is shown wherein an indication system 1110 for identifying the different uses of the retractor during a surgical procedure is embedded in the device. The present invention also provides a medical device that does not include all of the features of the first aspect, but which is characterized by the indication system as described above.

In another aspect, the present invention also provides a medical device that does not include all of the features of the first aspect, such as for example, does not necessarily comprise a control element, but which is characterized by the presence of a winding system with at least two spools, each of the spools being adapted for winding of an elongated wire-shaped element, wherein the spools are provided with a force element for the automatic winding of the elongated wire-shaped elements in order to bring it under tension, so that a tensile force is induced from two different directions. This system allows to apply a differential force on the retractor. Further optional components and features, as well as alternative mechanical retracting systems, can be as described in the first aspect.

Figure 5:
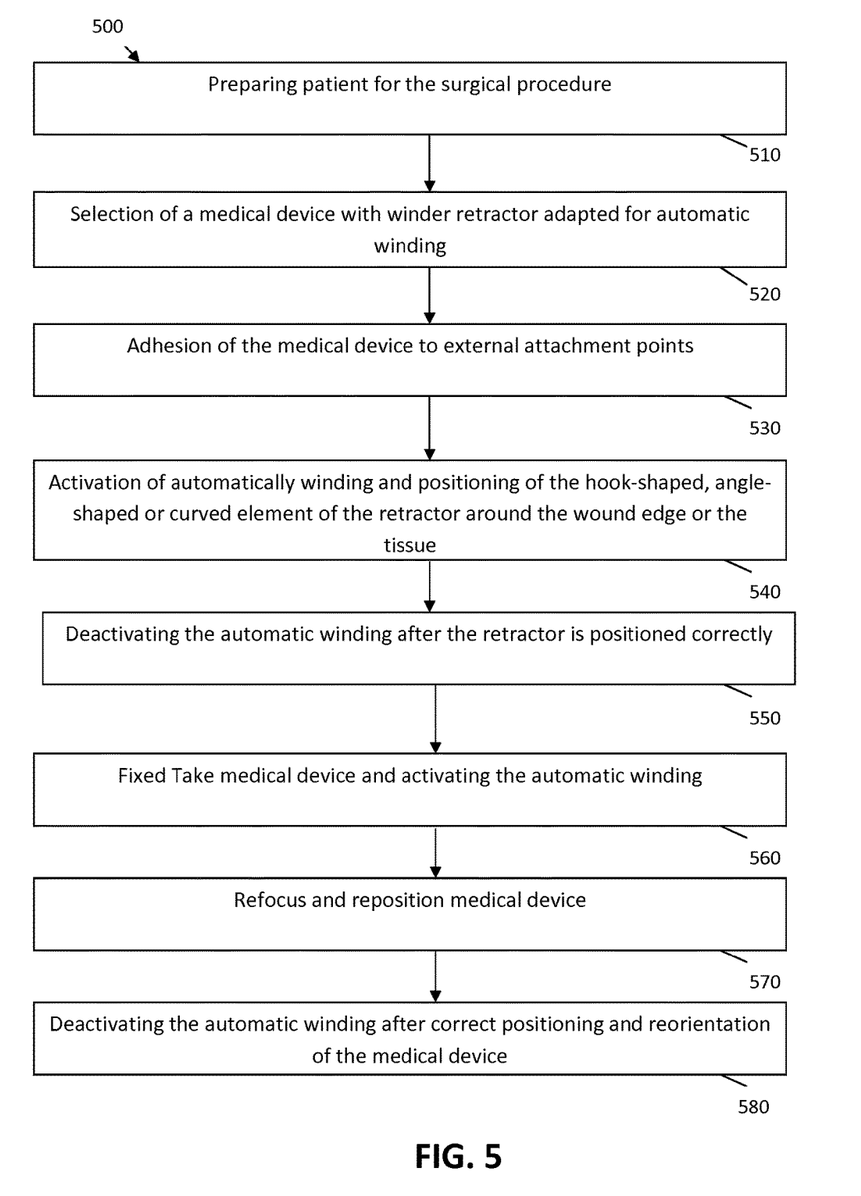
FIG. 5 illustrates a schematic overview of a method for retracting an incision for keeping open a wound, according to one embodiment of the present invention.

In a second aspect, the present invention relates to a method for keeping open a wound during surgery. The method may advantageously be used when one or more medical devices are used as described in the first aspect. By way of example, embodiments of the present invention not being limited thereto, a method according to an embodiment of the present invention will be described with reference to FIG. 5. The method 500 for keeping open a wound during surgery, as shown in FIG. 5 includes standard and optional steps.

In a first step 510, the patient is prepared for the surgical procedure. Although this step is essential for the surgical procedure itself, this step is not essential for the method for keeping open the wound, and this step can be carried out in advance. In a particular embodiment, this may be performed using a surgical drape for covering the patient. The surgical drape may, for example, be as described elsewhere in this description.

In a second step 520, a medical device comprising a retractor with winding system, e.g. as described in the first aspect, is selected. Such a medical device may take the form of an example, embodiment and/or a device according to the general principle of the first aspect. It may have or comprise a combination of elements from examples, embodiments and/or devices according to the general principles indicated of the first aspect.

In a third step 530, the medical device is fixed to at least one external fixation point. This may be to the patient, to a drape with integrated fixation points, to external objects or fixing means such as brackets or mountings, to the operation table, etc. Fixing the medical device typically is done by fixing one end of the elongated wire-shaped element to attach to the external fixing point. If there is initially too little elongate wire-like element available, the available wire-like element can be prolonged by activating the control element, and by making available wire-shaped element by applying a pulling force on the elongated wire-shaped element. In preferred methods, the medical device comprises more than one spool, and the medical device is fixed to more than one external fixation point. By making use of multiple elongate wire-like elements a differential force or tension can be applied to the medical device, allowing to provide a particular orientation of the medical device. The latter can, using embodiments of the present invention, be performed in a smooth manner.

In a fourth step 540, the method comprises the activation of the automatic winding and the positioning of the element, e.g. hook-shaped, angle-shaped or curved element, of the retractor to hold the edge of the wound or the surrounding tissue, so that the retractor is positioned in the appropriate orientation. The user thereby typically can grasp the medical device in the hand, control the control element so that the automatic winding is activated and the elongate wire-like elements are brought under tension by the automatic winding. The element, e.g. hook-shaped, angle-shaped or curved element, is positioned around the edge of the wound or tissue. In this way, the medical device, more specifically, the retractor is correctly positioned.

In a fifth step 550, the method includes the deactivation of the automatic winding after the retractor is correctly positioned. In this manner, the elongate wire-like elements are fixed to the preferred length. The person handling the retractor can then put release the retractor.

Further, during surgery, also a re-orientation of the refractor can be carried out. For this purpose, the method can comprise a sixth step 560 wherein the medical apparatus is again grasped, and the automatically winding is activated by the use of the control element.

In a seventh step, the medical device 570 is then reoriented as required. In an eighth step 580, after the correct reorientation of the medical device, the deactivation of the automatic winding takes place, and the retractor can again be released.

When positioning of one or more medical devices for keeping open a wound as described above, in some embodiments, an indication system can be used that provides information about the use of the one or more medical devices at a given step in the surgical process. Such indication can be adjusted manually or automatically, e.g. using a counter or an indication indicating the current step in the surgical process.

The method may also comprise further optional steps, for example steps that partially or fully express the functionality of one or more elements described in the first aspect.

In a further aspect, the present invention also relates to a mechanical retracting system, e.g. a mechanical winding system, adapted for connecting to a medical retractor with an external fixation point for keeping open a wound or incision during surgery. The mechanical retracting system can be coupleable to or forming part of the medical retractor. The mechanical retracting system may comprises a force element for automatically retracting an elongate wire-like element to apply tension thereto. In some embodiments, the mechanical retracting system may be a winding system that comprises at least one spool for winding an elongated wire-shaped element, wherein the at least one spool is provided with a force element for the automatic winding of the elongated wire-shaped element to apply tension to it. The mechanical retracting system advantageously is provided with at least one control element for activating/deactivating the automatic retracting. The mechanical retracting system, e.g. winding system may further comprise one or more characteristics of the mechanical retracting system as described in embodiments of the first aspect.

In another aspect, the present invention relates to a set of medical devices for keeping open a wound during surgery, wherein at least one of the medical devices is a medical device according to an embodiment of the first aspect. The other medical devices may for example be standard retractors. One of the medical devices can for example be a retractor with refracting system, e.g. winding system, whereby—in operation—the refractor and retracting system are typically configured so that the refracting system is closer to the external fixation point than to the retractor. The set of medical devices may also include a surgical drape, as described below. Further features and advantages of the set of medical devices may be the same or similar to those shown in the other aspects of the present description.

In a further aspect, the present invention relates to a surgical drape for sterile covering of the abdomen and legs for a surgical procedure. The surgical drape, according to embodiments of this aspect of the present invention, can advantageously be used for hip surgery, surgery of the knees, surgery of the inguinal region, surgery of the abdomen or of the abdomen region. A specific example of surgery where the surgical drape can advantageously be applied is hip surgery according to the direct anterior approach (DAA), embodiments of this aspect of the present invention not being limited by this.

According to embodiments of the present invention, the surgical drape comprises a first portion provided with two legs and a second portion provided with an incision window, wherein the second portion is arranged with respect to the first portion that the incision window covers at least partly, and advantageously completely, the abdomen region and the inguinal region, when the legs—e.g. upper legs—of a patient that needs to undergo the surgery are positioned in the leg-shaped portions of the surgical drape. By way of illustration, embodiments of the present inventions not being limited thereby, an example according to an embodiment of this aspect of the present invention is discussed, referring to FIG. 6.

Figure 6:
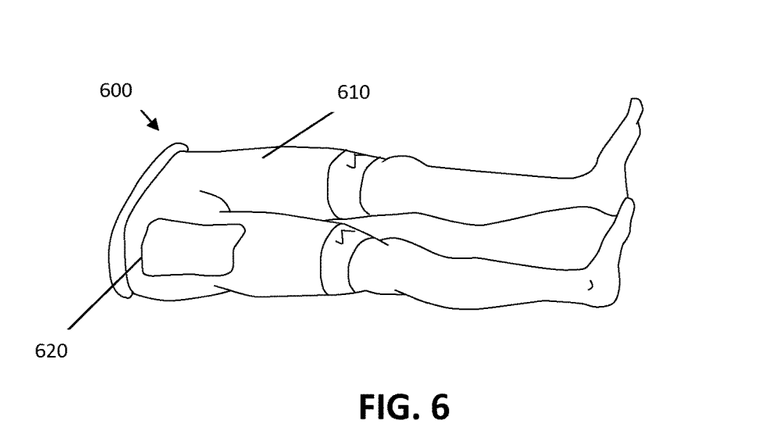
FIG. 6 illustrates a surgical drape, according to an embodiment of another aspect of the present invention.

A surgical drape 600 is shown provided with a first part 610, which includes two leg-shaped portions. In this way, with a single cloth, both legs of the patient can be covered. The leg-shaped portions can be manually unrolled, e.g. once the legs have been inserted in the leg-shaped portions. Alternatively, the surgical drape 600 can be fitted with an automated system, for example provided on the inside of the leg-shaped portions, so that the cloth can be automatically unrolled. The leg-shaped portions can e.g. be unfold telescopically. The surgical drape 600 also includes a second portion 620 comprising an incision window that covers, when in position, at least part of the inguinal region and abdomen. The incision window can be provided in a region of the drape corresponding with the full abdomen or corresponding with both sides of the body, so that drapes are provided that can be used for different sides of the body. Alternatively, incision windows can be provided such that the same drape can be used for surgery on different parts of the body. Because this incision window is provided in the surgical drape that also allows covering the legs, the action of covering legs and providing an incision window can be completed in the same step. The second part, which is also sometimes referred to as the upper abdomen flap, may, in some embodiments, be adapted in size so that it can further be unfolded to cover the sides of the patient and the portion up to the thorax or even further. In a specific embodiment, openings may be provided at the side of the second portion for providing fixation elements through it. Such openings may for example be telescopic windows wherein the fixation elements such as rods can be inserted, the fixation elements further also being connectable to the operating table.

The surgical drape may, in certain embodiments, also comprise a third, optional, part that sometimes is referred to as the foot flap, and that, for example, initially is attached to the rear side of the leg-shaped portions. This flap can be partly detached so that it can be unfold towards or over the feet. This part can be used as a protection layer.

An optional fourth part of the surgical drape may be provided to the upper abdomen flap or to the foot flap, which can be unfolded to the side so that the upper abdomen flap and the foot flap may be hermetically connected to each other.

In a specific embodiment, the surgical drape therefore is a drape with four parts, i.e. a part with leg-shaped portions (also referred to as pants), an abdomen flap with an incision window at the level of the abdomen and with a telescopic side portion for the provision of external fixation elements, and a foot part to which a part is connected for hermetically connecting the abdominal portion and the foot part.

Using such a surgical drape, the patient is entirely covered on all sides and, in addition, the legs are integrated into the fabric so that the legs can freely be moved during the surgical procedure.

It is an advantage according to embodiments of this aspect of the present invention that the risk of sterilization errors is low, as the surgical drape can cover in a few movements the inguinal region and abdomen in a sterile manner.

It is an advantage according to embodiments of this aspect of the present invention, that fewer steps, less time, and less manpower is required in order to cover a patient in a sterile manner.

It is an advantage according to embodiments of this aspect of the present invention, that the specific shape of the surgical drape allows manipulating the legs of the patient freely, while the risk of sterilization errors is largely reduced.

Figure 7:
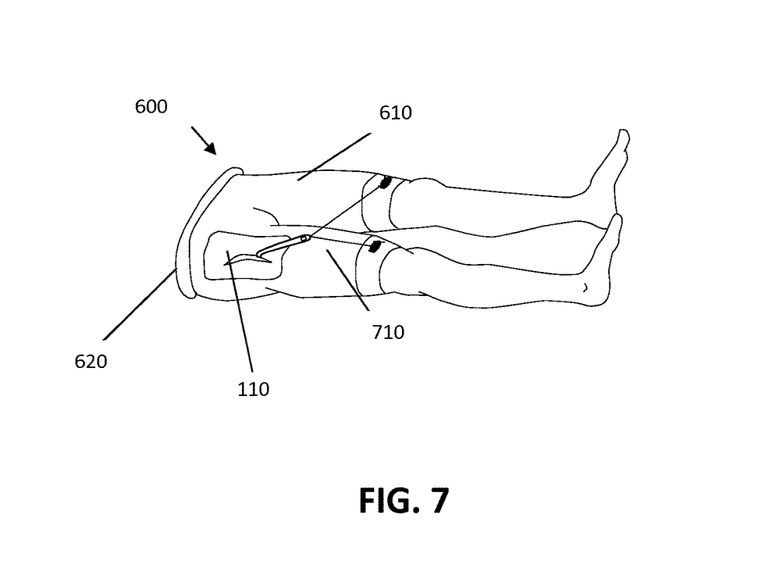
FIG. 7 illustrates a surgical drape with integrated fixation points in accordance with an embodiment of another aspect of the present invention.

In a specific embodiment of the present invention, the surgical drape comprises integrated fixation points 710, as shown in FIG. 7. These integrated fixation points 710 allow the surgeon or the assisting personnel to fix one or more retractors or attributes to the drape. By linking the retractors or attributes to the integrated fixation points 710 in the drape, the incision or wound can be kept open.

In a particular embodiment, the integrated fixation points 710 in the surgical drape can be position near the leg-shaped portions. This allows to couple one or more retractors to the leg-shaped portions, which retractors then can be oriented by the movement of the legs of the patient. In this particular embodiment, both the surgical drape as well as the legs of the patient become part of or assist in the retracting system.

It is an advantage of embodiments of this aspect of the present invention that the legs can be used for assisting for keeping the wound or incision open, as the legs of the patient can be moved freely and as the retractors are connected to these freely moveable legs. By moving the legs, also the retractors change their position and the wound in the patient is kept open in a specific way.

It is an advantage of embodiments of this aspect of the present invention that it allows smooth and quick keeping open of the wound, and that the surgery can take place fluently without any additional costs, such as for a specific surgery tables or additional personnel.

It is an advantage of embodiments of this aspect of the present invention that the integration of a number of integrated fixation points 710 ensures that less handling is required to create fixation points for the retractors, but also that the retractors can easily be fixed to the surgical drape and the legs and that the surgical drape, the patient and the retractors form together a full system for keeping open wounds, e.g. a self-retracting system for keeping open wounds.

In a specific embodiment, integrated fixing points also are provided in the upper abdomen flap. The tensile stress caused by retractors attached to these fixation points can, for example, be compensated by coupling the upper abdomen part to fixation elements, such as rods which can be inserted through openings provided in the abdomen flap as described above. Alternatively, the retractors can also be directly attached to rods which pass through the upper abdominal flap and which are connected e.g. to the surgical table. Also in this embodiment, an efficient system is obtained, whereby additional personnel costs can be avoided or the available personnel can be used for other actions than assisting in the wound retracting action. As the number of retractors to be used also decreases, this also provides a possible reduction in transport costs, sterilization costs, logistics costs, etc.

It is an advantage of embodiments according to the present invention that the use of a surgical drape that combines leg-shaped portions with an incision window allows significant reduction in the time required for covering a patient.

It is an advantage of embodiments according to the present invention that the integrated fixation points 710 in the surgical drape can be provided in such a way that relatively large forces can be tolerated. The latter can be obtained by integrating the fixation points at or near positions where the surgical drape is attached to an external reference point such as the leg-shaped portions that are connected to the legs of the patient or the surgical drape being fixed to external fixation elements such as support poles or tripods.

In one aspect, embodiments of the present invention also concerns the use of a surgical drape as described above for preparing a patient for a surgical procedure. In another aspect, embodiments of the present invention also relate to the use of a surgical drape with an integrated fixing points for keeping open a wound during a surgical procedure.

The various aspects can be easily combined with each other, and the combinations thus also correspond with embodiments according to the present invention.

The invention claimed is:

1. A medical device for keeping open a wound during surgery, the medical device comprising:
   a surgical retractor provided with an element for placing at an edge of a wound or tissue;

a mechanical retracting system, wherein the mechanical retracting system comprises at least one spool for winding an elongate wire-like element,
   the elongate wire-like element capable of being wound at the at least one spool, and
   a force element for automatically retracting the elongate wire-like element to apply tension to the elongate wire-like element;
wherein the mechanical retracting system is arranged for forming part of the retractor or for coupling to the retractor such that the spool is positioned between the element for placing at the edge of the wound or tissue and an unwound portion of the elongate wire-like element.

2. A medical device according to claim 1, wherein the mechanical retracting system is provided with at least one control element for activating and/or deactivating the automatic retracting.

3. A medical device according to claim 2, wherein the at least one control element comprises a control point on the retractor or on the mechanical retracting system for activating/deactivating the automatic retracting and/or wherein the control element comprising at least one of the group of a clamp for clamping the elongate wire-like element, a blocking element that interferes with a spool or the force element, for preventing automatically winding or a coupling mechanism for detachably coupling the force element and a spool.

4. A medical device according to claim 1, wherein the retracting system comprises a differential retracting system.

5. A medical device according to claim 1, wherein the mechanical retracting system is a mechanical winding system, wherein the at least one spool is provided with the force element for automatically winding the elongate wire-like element to apply tension to the elongate wire-like element.

6. A medical device according to claim 5, wherein the winding system comprises more than one spool, each spool being configured for winding an elongated wire-like element for connecting the winding system to an external fixation point, so that by the use of more than one spool, an orientation of the retractor with respect to the wound can be controlled.

7. A medical device according to claim 6, wherein the winding system comprises for each spool a force element.

8. A medical device according to claim 6, wherein at least one control element is arranged for simultaneously controlling the automatic winding of different spools or wherein the at least one control element comprises a set of control elements, each control element being adapted for controlling the automatic winding of a spool.

9. A medical device according to claim 1, wherein the force element is a torsion spring or a micro-electromechanical system.

10. A medical device according to claim 1, wherein the mechanical retracting system and the surgical retractor are two distinct elements which can be coupled to one another and which together form a kit of parts of the medical device.

11. A medical device according to claim 1, wherein the surgical retractor and the mechanical retracting system each have a coupling element for detachably coupling to one another.

12. A medical device according to claim 1, wherein the mechanical retracting system is embedded in the surgical retractor and/or wherein the medical device furthermore comprising an indication mechanism for indicating information regarding the use of the surgical retractor during a set of successive steps of a surgical procedure.

13. A medical device according to claim 12, wherein the indication mechanism is configured for indicating whether for a particular step, the surgical retractor is to be used, the surgical retractor is to be used in combination with another surgical retractor, an orientation wherein the surgical retractor is to be used and/or which external fixation points are to be used.

14. A medical device according to claim 1, wherein
   the mechanical retracting system comprises at least a spool for winding the elongated wire-like element that can connect the mechanical retracting system to an external fixation point and/or wherein the element for placing at an edge of a wound or tissue is a hook shaped, angle shaped or curved element for placing around an edge of a wound or tissue, or wherein the element comprises an engaging means for engaging with an edge of a wound or tissue, and/or wherein the mechanical retracting system comprises a housing for containing the at least one spool, and the housing comprises an opening through which the elongated wire-like element can pass.

15. A method for keeping open a wound during surgery, the method comprising
   selecting a medical device according to claim 1,
   fixing the medical device to at least one external fixation point,
   activating the automatic retracting and positioning the element for placing at an edge of a wound or tissue of the retractor at an edge of the wound or the tissue, and
   de-activating the automatic retracting after the retractor is positioned correctly.

16. A method according to claim 15, wherein the method further comprises
   handling the medical device and activating automatically winding,
   re-orienting the medical device,
   after re-orienting the medical device correctly, deactivating the automatic retracting and releasing the retractor.

* * * * *